United States Patent

Richards

(10) Patent No.: US 12,268,624 B1
(45) Date of Patent: Apr. 8, 2025

(54) KAFO FULL LEG BRACE FOR PREVENTING KNEE BUCKLING

(71) Applicant: Dennis James Richards, St. Charles, MO (US)

(72) Inventor: Dennis James Richards, St. Charles, MO (US)

(*) Notice: Subject to any disclaimer, the term of this patent is extended or adjusted under 35 U.S.C. 154(b) by 613 days.

(21) Appl. No.: 17/734,110

(22) Filed: May 1, 2022

Related U.S. Application Data

(63) Continuation-in-part of application No. 16/161,616, filed on Oct. 16, 2018, now abandoned.

(60) Provisional application No. 62/576,054, filed on Oct. 23, 2017.

(51) Int. Cl.
*A61F 5/01* (2006.01)

(52) U.S. Cl.
CPC .......... *A61F 5/0125* (2013.01); *A61F 5/0111* (2013.01); *A61F 2005/0181* (2013.01)

(58) Field of Classification Search
CPC ................ A61F 5/0125; A61F 5/0111; A61F 2005/0181; A61F 5/0123; A61F 5/0102; A61F 5/01; A61F 5/00; A61F 5/0127; A61F 5/0104; A61F 5/0113; A61F 5/0106
See application file for complete search history.

(56) References Cited

U.S. PATENT DOCUMENTS

| 2,516,253 | A | * | 7/1950 | Pieterick | A61F 5/0102 403/62 |
| 4,088,130 | A | | 5/1978 | Applegate | |
| 5,094,232 | A | | 3/1992 | Harris et al. | |
| 5,133,341 | A | | 7/1992 | Singer et al. | |
| 5,277,698 | A | | 1/1994 | Taylor | |
| 5,400,806 | A | | 3/1995 | Taylor | |
| 5,458,565 | A | | 10/1995 | Tillinghast, III et al. | |

(Continued)

FOREIGN PATENT DOCUMENTS

| CN | 112603621 A | * | 4/2021 | ........... A61F 5/0104 |
| EP | 2932944 B1 | * | 12/2019 | ........... A61F 5/0113 |
| EP | 4201380 A1 | * | 6/2023 | ........... A61F 5/0111 |

OTHER PUBLICATIONS

C-Brace Leg Orthosis [online]. Ottobock, Apr. 28, 2022. Retrieved from the Internet: <URL: https://www.ottobockus.com/orthotics/solution-overview/c-brace/>.

(Continued)

*Primary Examiner* — Tarla R Patel
(74) *Attorney, Agent, or Firm* — Carmody MacDonald P.C.; Dennis J M Donahue, III; Kevin C. Staed

(57) ABSTRACT

The invention is a knee ankle foot orthosis for controlling and preventing knee buckling through an innovative stirrup that is fixedly connected at its proximal section to the anterior inferior segment of the orthosis' calf engaging section. The stirrup has a twisted section between its proximal and distal sections so the proximal section is in a coronal plane while the distal section is in a sagittal plane and connects to the lateral side of the footplate. The stirrup's proximal section does not rotate relative to the calf engaging section while the distal end of the stirrup bends relative to the proximal end of the stirrup, thereby storing energy like a leaf spring when it is bent. The bent stirrup applies a posterior directed force in the sagittal plane to the orthosis' calf engaging segment to prevent knee buckling during the mid-stance segment of the gait cycle.

20 Claims, 9 Drawing Sheets

(56) References Cited

U.S. PATENT DOCUMENTS

| | | | |
|---|---|---|---|
| 6,969,364 B2 | 11/2005 | Sterling | |
| 7,201,728 B2 | 4/2007 | Sterling | |
| 8,292,838 B2 | 10/2012 | Ingimundarson et al. | |
| 8,764,692 B2 | 7/2014 | Ferrigolo et al. | |
| 9,022,965 B2 * | 5/2015 | Auberger | A61F 5/0125 |
| | | | 602/26 |
| 2004/0068215 A1 | 4/2004 | Adelson et al. | |
| 2004/0267179 A1 | 12/2004 | Lerman | |
| 2008/0300525 A1 | 12/2008 | Shlomovitz | |
| 2011/0105969 A1 * | 5/2011 | Nace | A61F 5/34 |
| | | | 602/26 |
| 2018/0256380 A1 | 9/2018 | Pusch et al. | |

OTHER PUBLICATIONS

Sharmana Ghosh, Nina P. Robson & J. Michael McCarthy, Kinematic Design and Evaluation of a Six-Bar Knee-Ankle-Foot Orthosis, Journal of Engineering and Science in Medical Diagnostics and Therapy, May 2020, vol. 3 / 021111-1, US. Retrieved from the Internet: <URL: https://par.nsf.gov/servlets/purl/10194734>.

3D Printed Leg Brace [online]. Braceworks, Jun. 4, 2015. Retrieved from the Internet: <URL: https://braceworks.ca/2015/06/08/health-tech/perfect-fit-3d-printed-leg-brace/>.

Dynamic KAFO Brochure [online]. Thuasne, Apr. 28, 2022. Retrieved from the Internet: <URL: https://www.thuasneusa.com/wp-content/uploads/2020/12/Dynamic-KAFO_Web.pdf>.

\* cited by examiner

KAFO FULL LEG BRACE FOR PREVENTING KNEE BUCKLING

CROSS-REFERENCE TO RELATED APPLICATIONS

This application is a continuation-in-part of U.S. patent application Ser. No. 16/161,616 filed on Oct. 16, 2018 which claims priority from U.S. Provisional Patent Application No. 62/576,054 filed on Oct. 23, 2017, both of which are hereby incorporated by reference.

STATEMENT REGARDING FEDERALLY SPONSORED RESEARCH

Not Applicable.

APPENDIX

Not Applicable.

BACKGROUND OF THE INVENTION

Field of the Invention

The present invention relates to full leg braces, and more particularly to knee ankle foot orthosis (KAFO) devices for controlling knee buckling using dynamic energy from movement of the foot and ankle.

Related Art

It is known to use KAFOs for treating patients that suffer from instability of the foot and ankle and buckling of the knee. KAFOs for controlling knee buckling are fabricated from bulky and rigid carbon fiber, metal, or plastic with a double or single hinge with a mechanical apparatus incorporated in the knee joint on the KAFO. One problem with these KAFO is the materials used and profiles of the orthosis are extremely rigid and bulky, making the KAFO difficult to don and doff as well as uncomfortable for the wearer. Of course, with the increased size and bulk, common KAFO are also overly heavy which further adds to the wearers discomfort and increases the chances that the patient will abandon wearing the orthosis altogether. Further, generally known KAFOs that are designed to lock and unlock automatically, called stance control orthosis, are even more rigid and bulky due to the sophisticated mechanical locking feature that is included in the knee hinge of the orthosis. Even still, most of the KAFOs that have a mechanical locking feature are designed for treating knee buckling in addition to foot drop and knee hyperextension. Although they are effective at controlling knee buckling, patients tend to have a stiff leg gait pattern. Further, patients typically abandon these due to difficulty locking or unlocking the knee mechanism or from expending too much energy ambulating with stiff leg pattern. This stiff leg gait pattern can increase fall risk due to the inability to flex the knee when advancing the leg. Accordingly, there is a desire to have an improved KAFO capable of controlling knee buckling in a patient's knee without a locking mechanism at the knee or ankle.

It is well known that knee buckling affects millions of people, especially those 65 and over. These patients will be looking for lighter and more cosmetically accepted orthosis designs. However, existing KAFOs that control knee buckling all use some type of mechanical locking feature, whether on the knee joint or at the ankle, which increases the weight and stiffness of the devices. In the prior art, KAFOs that cross the knee and ankle without a knee locking mechanism are designed to control foot drop, knee hyper extension, *varus*/valgus conditions and other deformities, but not for preventing knee buckling. Accordingly, there is a large desire to provide an improved KAFO capable of treating knee buckling that is light weight, comfortable and cosmetically appealing. It would be particularly beneficial if the improved KAFO could accomplish these benefits while eliminating the use of any type of mechanical locking feature.

Successful outcomes in treatment of knee buckling is largely patient dependent and thus a need exists in the art for a comfortable and easy to use KAFO that increases the likelihood that the patient will actually wear the orthosis. The patients who have a relatively normal height and weight proportional lower extremity typically have better outcomes whereas patients that fall outside this range tend to abandon their KAFOs. In a population-based study of 2,351 men and women with a median age of 63.5 years, ten percent (10%) of all adults experienced knee buckling and four (4) out of five (5) bucklers had knee pain. In this population, there are individuals who have different heights and weights which directly impacts the treatment, but there has not been any KAFO design criteria developed for different weights and sizes.

Accordingly, it has long been desired to produce an orthosis that leads a patient having a more stable knee with less pain. It would be particularly beneficial to create KAFO devices based on a design criteria that provides for a more stable knee with less pain for a range of different weights and sizes of patients so that more patients are compliant in their use of the KAFO rather than abandoning the KAFO.

During the middle of the stance phase of the gait cycle (i.e., mid-stance), when all the weight is on a single limb, the only muscle group firing is the triceps surae which includes the gastronomic muscle and the soleus muscle. The gait cycle is graphically shown in FIG. 1. It is at this point when these muscles are pulling back on the tibia and eccentrically controlling the momentum and inertia of the body weight. When these muscles are weak, the ankle will give out and induce a collapse of the ankle joint. Because this event happens in a closed chain, once the ankle collapses the knee joint follows and then the knee buckles. The knee buckles because of what happens at the ankle joint. For the average person, the quadriceps and hip extensors and mostly the triceps surae muscle group can activate quickly to prevent falls by providing stumble control and stability. However, those patients who suffer from a weakness specifically in the triceps surae muscle group will demonstrate problematic knee buckling episodes.

To solve this known problem, it would be beneficial to incorporate a fixed but flexible stirrup within the KAFO to passively store energy from the person's gait and then transfer and redirect the force with the correct amount of dynamic force to prevent the knee buckling. Prior art KAFOs have stirrups that are too stiff and unable to flex in the sagittal plane during the mid-stance of the gait as required to store energy for controlling knee buckling. The prior art designs only flex and store energy at the end of stance at toe off, but this phase of the gait cycle doesn't have any effect on knee buckling because at this point in the gait cycle, the opposite heel is in contact with the ground or referred to as double stance.

SUMMARY OF THE INVENTION

The invention is a knee ankle foot orthosis (KAFO) for treating and preventing knee buckling through an innovative joint integrated with the superior thigh engaging section and inferior calf engaging section of the orthosis with a stirrup that anteriorly and laterally crosses the ankle joint to provide a more rigid and sturdy orthosis that controls knee buckling without using any mechanical locking feature. In the preferred embodiment, the distal end portions of the thigh section and calf section have a curved shape which nest within one another and are operatively connected with a nut and bolt fastener. Further, a flexible washer is positioned between the nested distal ends to prevent sliding and unwanted movement within the joint.

In another aspect of the invention, the dynamic stirrup is a one piece carbon fiber stirrup which crosses the ankle joint just anterior of the lateral malleolus with a contoured carbon footplate holding the foot and thereby controlling knee buckling. The configuration may extend from the anterior medial or even from the posterior medial or lateral as long as the stirrup segment is aligned with the sagittal axis and bisects the tibia on the anterior aspect of the leg. This stirrup is attached anteriorly on the lower section of the orthosis to provide the posterior directed force generated from the ground up through the knee joints. The anterior attachment of the stirrup to the distal section of the orthosis is imperative to ease donning and to maintain proper alignment of the stirrup in relation to the tibia and the foot. The orthosis is made up of an upper section engaging the thigh of the patient and a lower section engaging a portion of the upper calf with the upper and lower sections connected by a single hinge or a pair of hinges at the knee joint on one side or on opposite sides of the knee, respectively.

The KAFO incorporates stored energy in the dynamic stirrup from movement during normal gait as a counter force for dynamic control around the knee and extension of the knee joint to control buckling during the middle of stance phase of the gait cycle. In particular, according to the design of the present invention, the stored energy in the stirrup is created by normal passive dorisflexion of the ankle which is then transferred and redirected to stabilize the knee.

Lastly, the state of prior art generally treats knee buckling and foot drop, but the prior art that treats buckling use mechanical locking systems. Additionally, there are many no KAFO devices that cross the ankle with a dynamic component to manage buckling of the knee. Accordingly, there is a desire to those having skill in the art to provide a KAFO that uses stored energy from the lower ankle and foot section to control knee buckling as well as providing a simplified joint at the knee to provide a generally sturdier and less complex KAFO with any locking mechanism.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

The invention is generally a knee ankle foot orthosis (KAFO) for treating random knee buckling by using energy storing dynamic sections and a stirrup that anteriorly and laterally crosses the ankle joint to connect to a footplate and provide an extension force to the knee during normal gait. The present invention uses an innovative hinge design that minimizes the parts for the hinge section of the orthosis with the energy storing stirrup between the orthosis sections and the footplate which eliminates the need for any locking mechanism and minimizes the bulkiness of the KAFO.

Figure 1:
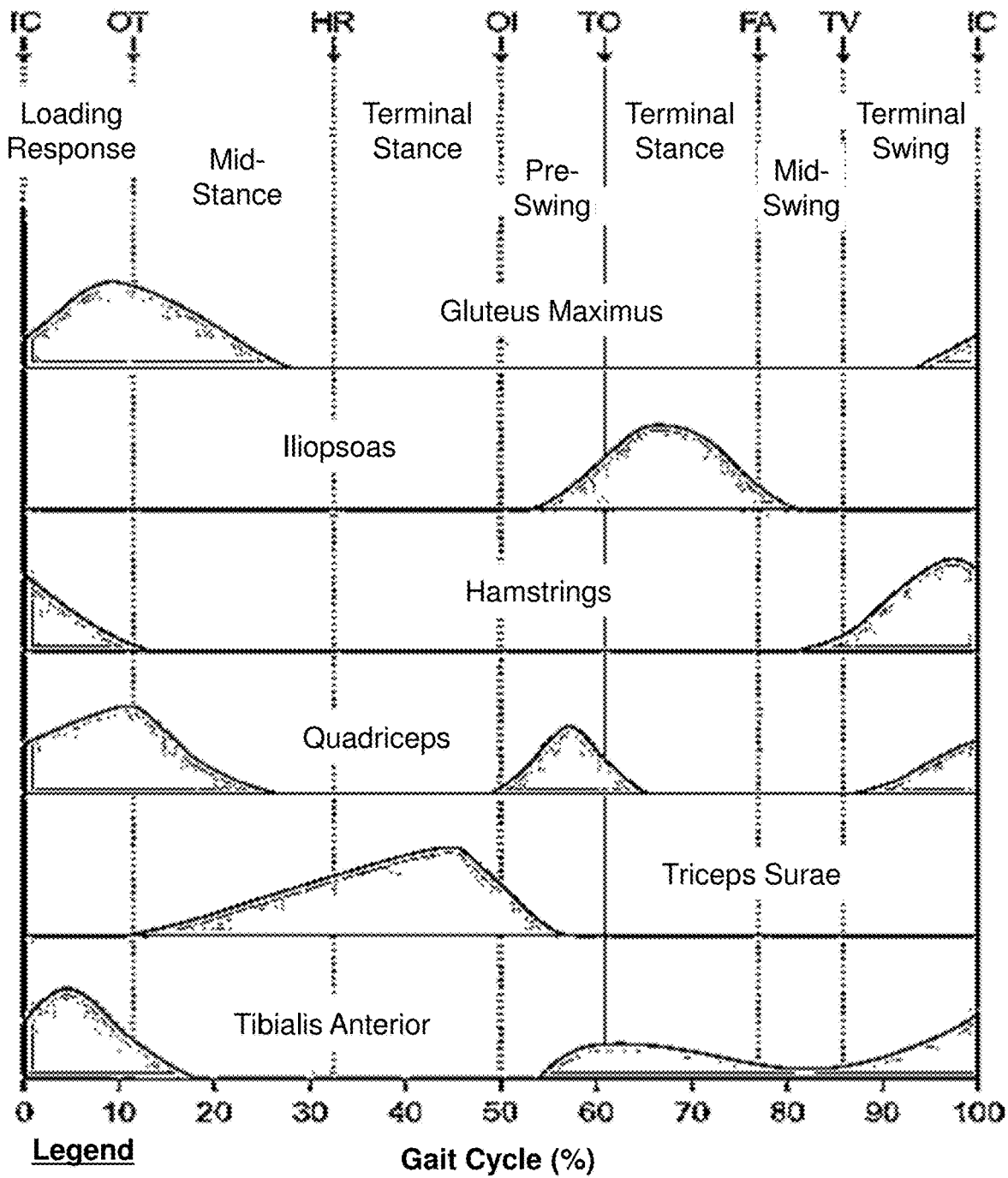
FIG. 1 is a graphical representation of a standard gait cycle.
Figure 2A:
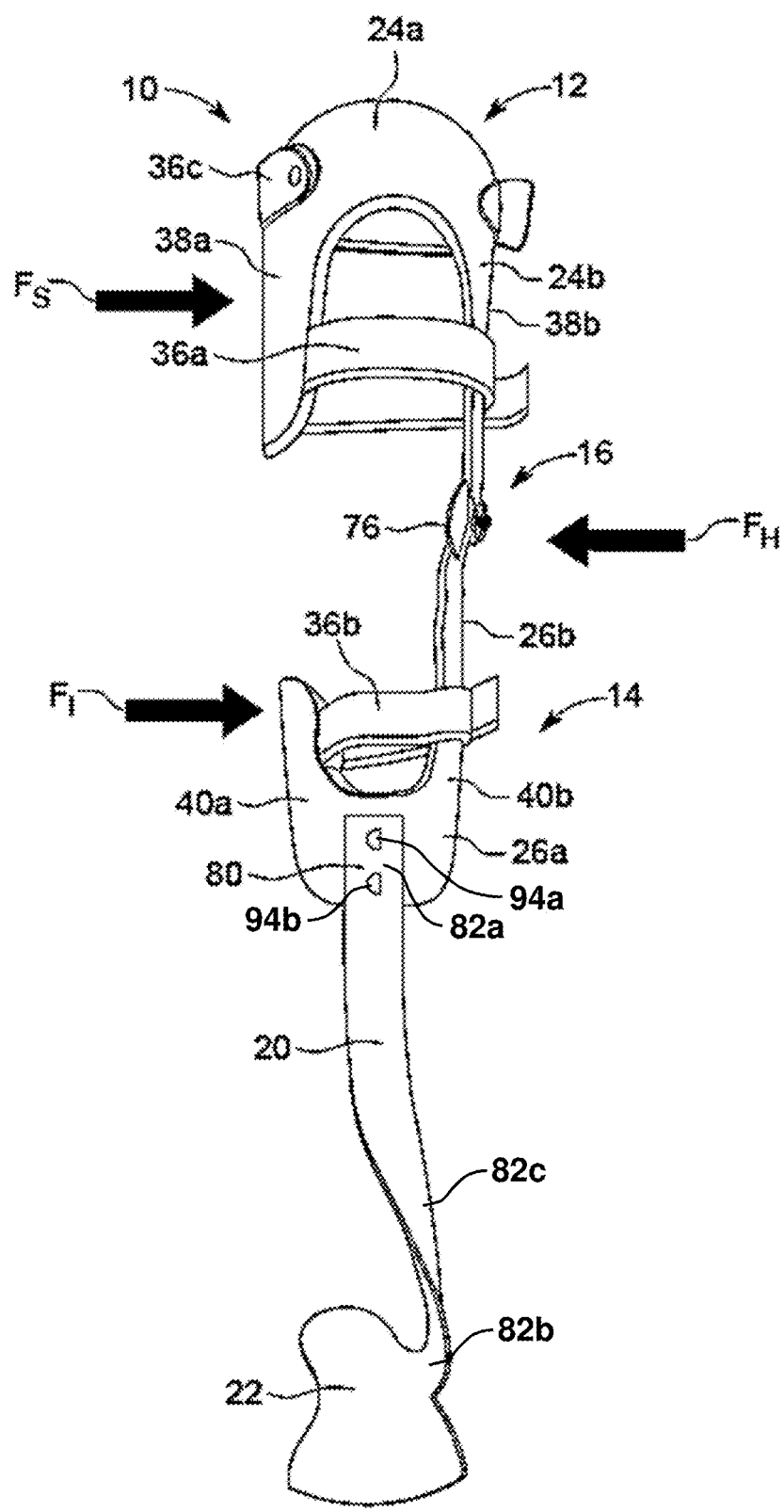
FIGS. 2A and 2B are front views of an orthosis with a stirrup and a footplate in a single hinge configuration and a double hinge configuration, respectively.
Figure 2B:
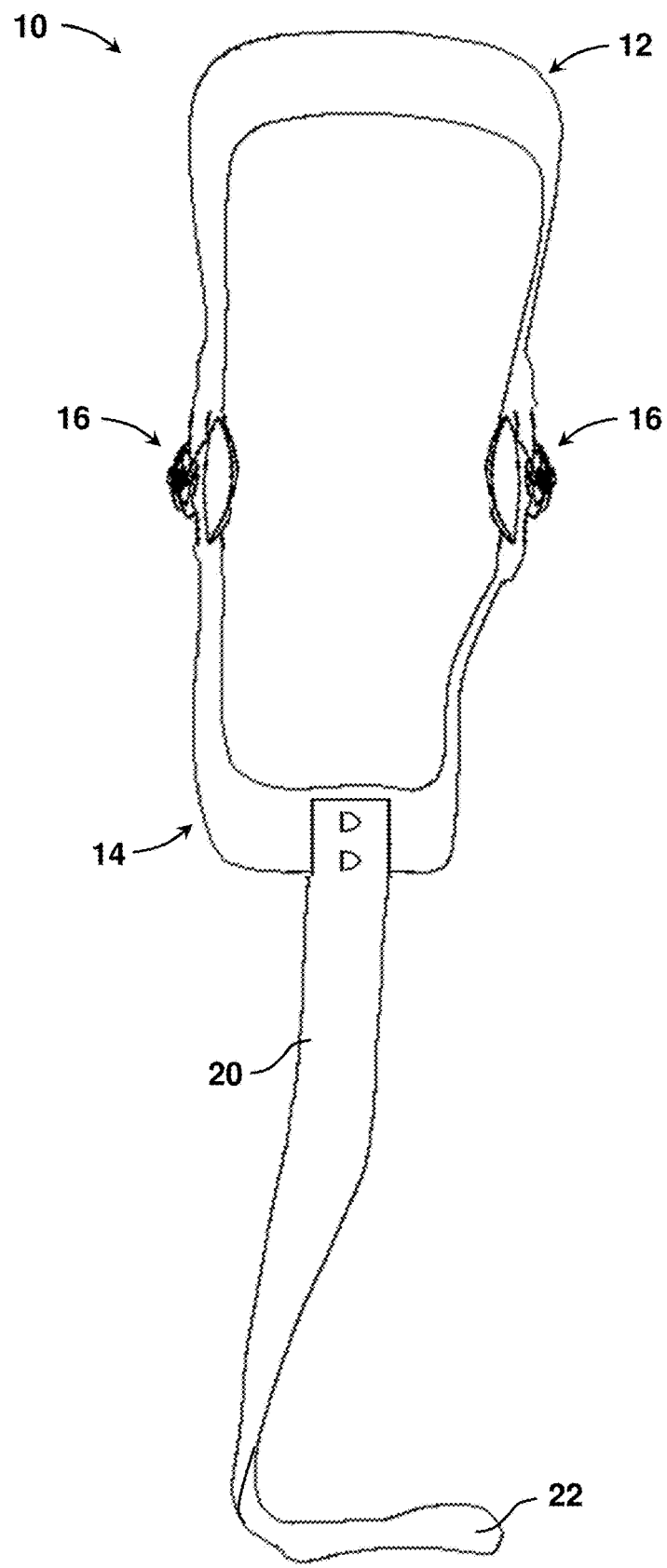

The hinged-joint portion of the orthosis 10 is positioned relative to the knee of a person with a thigh engaging section 12 positioned superior of the knee and a calf engaging section 14 positioned inferior of the knee. In operation, the thigh section and calf section are connected on one or both of the lateral and medial side of the knee by the joint 16 as shown in FIG. 2A and FIG. 2B, respectively. The stirrup 20 is securely fixed at its proximal end 82a to a mounting section 80 of the calf engaging section so that the stirrup cannot freely rotate relative to the orthosis. The footplate 22 is securely fixed to the stirrup's distal end 82b or may be formed integrally with the stirrup so that the stirrup's distal end cannot freely rotate relative to the stirrup. Between its fixed ends, the stirrup functions like a leaf spring, having flexibility in the sagittal plane during the mid-stance of the gait (i.e., moving between posterior and anterior positions), so that it stores energy for controlling knee buckling when it is bent. In particular, at the mid-stance, the footplate is firmly planted on the ground beneath the wearer's foot which fixes stirrup's distal end while the orthosis is moving forward with the person's leg which causes the proximal end of the stirrup forward and bending the flexible stirrup in the sagittal plane between its proximal and distal ends and producing a dynamic extension force that is stored within the stirrup as it is bent and is applied to the inferior anterior segment of the calf engaging segment as a posterior directed spring force in the sagittal plane during a mid-stance of a gait.

The correct amount of dynamic extension force in the stirrup is determined by fabricating the lower calf section the proper length and also the coupled with the proper length and stiffness of the stirrup. In addition, the fixed angle of the ankle must also be incorporated into the design. Other factors that will determine the stirrup stiffness are the person's height and weight, stride length and activity level. In optimizing the present invention, it has been determined that the forces to be generated by the stirrup are primarily based on the wearer's weight and the relative length of the stirrup ($L_S$) compared to the length of the orthosis' calf engaging section ($L_C$). In Table 1 below, the forces generated by the stirrup in the mid-stance part of the gait are tabulated relative to patient weights for different relative lengths of the orthosis' calf engaging section and the stirrup. In Table 2, the stirrup forces are normalized by the patient weights.

TABLE 1

| Patient Weight | Moment Generated by Stirrup (Nm) | | |
| --- | --- | --- | --- |
| (kg) | $L_C < L_S$ | $L_C \approx L_S$ | $L_C > L_S$ |
| 45 | 24 | 47 | 69 |
| 54 | 29 | 57 | 83 |
| 64 | 34 | 66 | 97 |
| 73 | 38 | 76 | 110 |
| 82 | 43 | 85 | 124 |
| 91 | 48 | 94 | 138 |
| 100 | 53 | 104 | 152 |
| 109 | 58 | 113 | 166 |
| 118 | 62 | 123 | 179 |

TABLE 2

| Patient Weight | Moment Normalized by Weight | | |
| --- | --- | --- | --- |
| (kg) | $L_C < L_S$ | $L_C \approx L_S$ | $L_C > L_S$ |
| 45 | 0.533 | 1.0444 | 1.5333 |
| 54 | 0.537 | 1.0556 | 1.5370 |
| 64 | 0.531 | 1.0313 | 1.5156 |
| 73 | 0.520 | 1.0410 | 1.5068 |
| 82 | 0.524 | 1.0365 | 1.5122 |
| 91 | 0.527 | 1.0329 | 1.5164 |
| 100 | 0.530 | 1.0400 | 1.5200 |
| 109 | 0.532 | 1.0366 | 1.5229 |
| 118 | 0.525 | 1.0423 | 1.5169 |

Figure 5A:
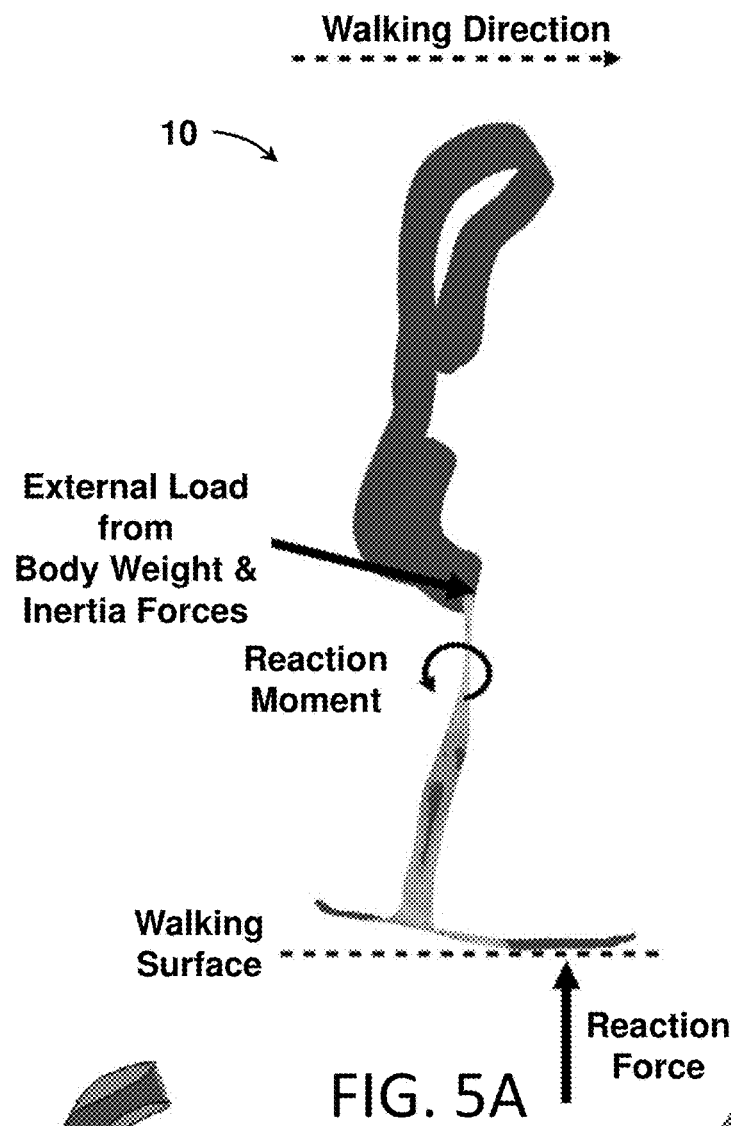
FIG. 5A is a graphic representation of the dynamic forces and moment imparted on the orthosis at the mid-stance of the gait.
Figure 5B:
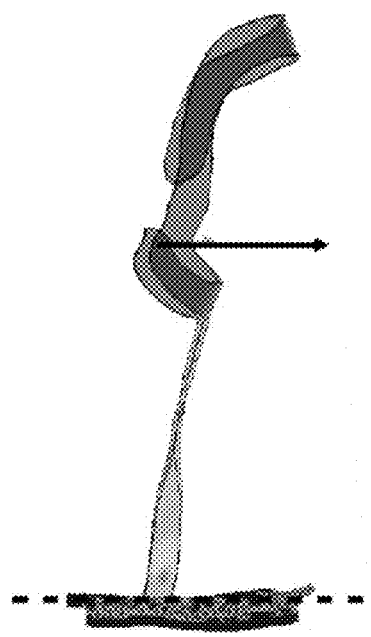
FIGS. 5B and 5C are graphic representations of the displacement of the orthosis relative to the footplate at the mid-stance of the gait for a stirrup that is longer than the lower orthosis assembly and for a stirrup that is shorter than the lower orthosis assembly, respectively.
Figure 5C:
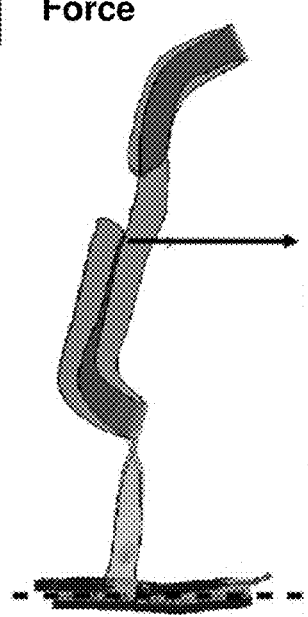

The dynamic forces and moment imparted on the orthosis at the mid-stance of the gait are graphically shown in FIG. 5A. The displacement of the orthosis relative to the footplate at the mid-stance of the gait is shown graphically in FIGS. 5B and 5C for a stirrup that is longer than the lower orthosis assembly ($L_S > L_C$) and for a stirrup that is shorter than lower orthosis assembly ($L_S < L_C$), respectively.

As shown in FIGS. 2 and 3, the thigh engaging section of the orthosis includes a superior anterior segment 24*a* positioned above an inferior side segment 24*b* having a distal end 44*a* that forms a portion of the joint opposite from the superior anterior segment. Additionally, the thigh section includes a medial superior side 38*a* and lateral superior side 38*b* which accommodate the adjustment straps 36 and flexible wrap 18 described in more detail below. The inferior side segment has a first longitudinal axis 42*a* extending between the superior anterior segment and a hole 46*a* in the center 50*a* of the circumferential distal end. Further, the distal end has a curved shape 54*a* having a convex outer surface 56*a* and corresponding concave inner surface 58*a* which nests with the distal end of the calf section described below.

Similar to the thigh engaging section, the calf engaging section is shown in FIGS. 2 and 3 and includes an inferior anterior segment 26*a* positioned below a superior side segment 26*b* with its distal end 44*b* forming another portion of the joint opposite from the inferior anterior segment. As with the thigh section, the superior side segment of the calf section has a longitudinal axis 42*b* between the inferior anterior segment and its distal end. Additionally, the calf section includes a medial inferior side 40*a* and lateral inferior side 40*b*. Further, the distal end of the superior side segment has a hole 46*b* at the center 50*b* of the distal end that aligns with the hole in the distal end of the inferior side segment on the thigh section, wherein the bolt extends through both holes when the orthosis is assembled. The distal end of the superior side segment also has a curved shape 54*b* with a convex outer surface 56*b* and corresponding concave inner surface 58*b*. Although it is preferred for the concave distal ends to be integrated with the respective side sections of the thigh and calf sections to limit the number of pieces in the joint assembly, it will be appreciated that the joint may be made from separate pieces and attached between the respective side sections of the thigh and calf sections.

To limit unintended movement in the joint between the thigh and calf sections of the orthosis, a flexible washer 28 is positioned between the conforming curved segments of the respective distal ends of the thigh engaging section and the calf engaging section. The flexible washer is preferably made from a plastic nylon structure that provides sufficient rigidity and sturdies the joint while simultaneously having low friction and allowing sufficient flexibility to allow the joint to hinge during normal gait. Additionally, the flexibility of the washer allows the washer to conform to the curvature of the distal ends of the thigh engaging section and the calf engaging section. Further, the washer also has a hole 46*c* at its center which aligns with the holes in the respective distal ends of the thigh engaging section and the calf engaging section to accommodate the bolt which holds the joint together.

To provide more rigidity and ensure the joint is secured when assembled, a rigid washer 30 is positioned on the external side 60 of the joint. The rigid washer has a curved shaped 62 conforming to the curved segments of the respective distal ends of thigh engaging section and the calf engaging section. Similarly, the washer also has a hole 46*d* at its center that aligns with the holes in the respective distal ends of the thigh engaging section and the calf engaging section and the flexible washer in order to accommodate the bolt which holds the joint together.

Accordingly, a bolt 32 having a head 64 and a shaft 66 extends through the holes in the distal end of the thigh engaging section, the distal end of the calf engaging section, the flexible washer and the rigid washer. In the preferred embodiment particularly shown in FIG. 4A, the head of the bolt engages the exterior of the rigid washer with the shaft extending thought the holes towards the internal sides 70 of the thigh engaging section and the calf engaging section. Conversely, it should be appreciated that head may engage the interior of one of the concave sides of the distal ends of the of the thigh engaging section and the calf engaging section and the shaft may extend through the aligned holes towards the rigid washer positioned on the exterior of the joint. Accordingly, the rigid washer can be positioned on either the internal or exterior side of the joint or in some cases may be used on both sides. In any case, the bolt allows the thigh engaging section and the calf engaging section to rotate relative to each other around the rotational axis 42c of the shaft.

To secure the bolt, a nut 34 is screwed onto the threaded distal end of the shaft 68a and in the preferred embodiment the nut is positioned against the internal side of either the thigh engaging section or the calf engaging section respective distal ends. As explained in regards to the bolt and washer above, it will be appreciated that the nut could be positioned on the external side of the joint in an alternative embodiment, although this arrangement is not shown in the drawings.

Figure 4A:
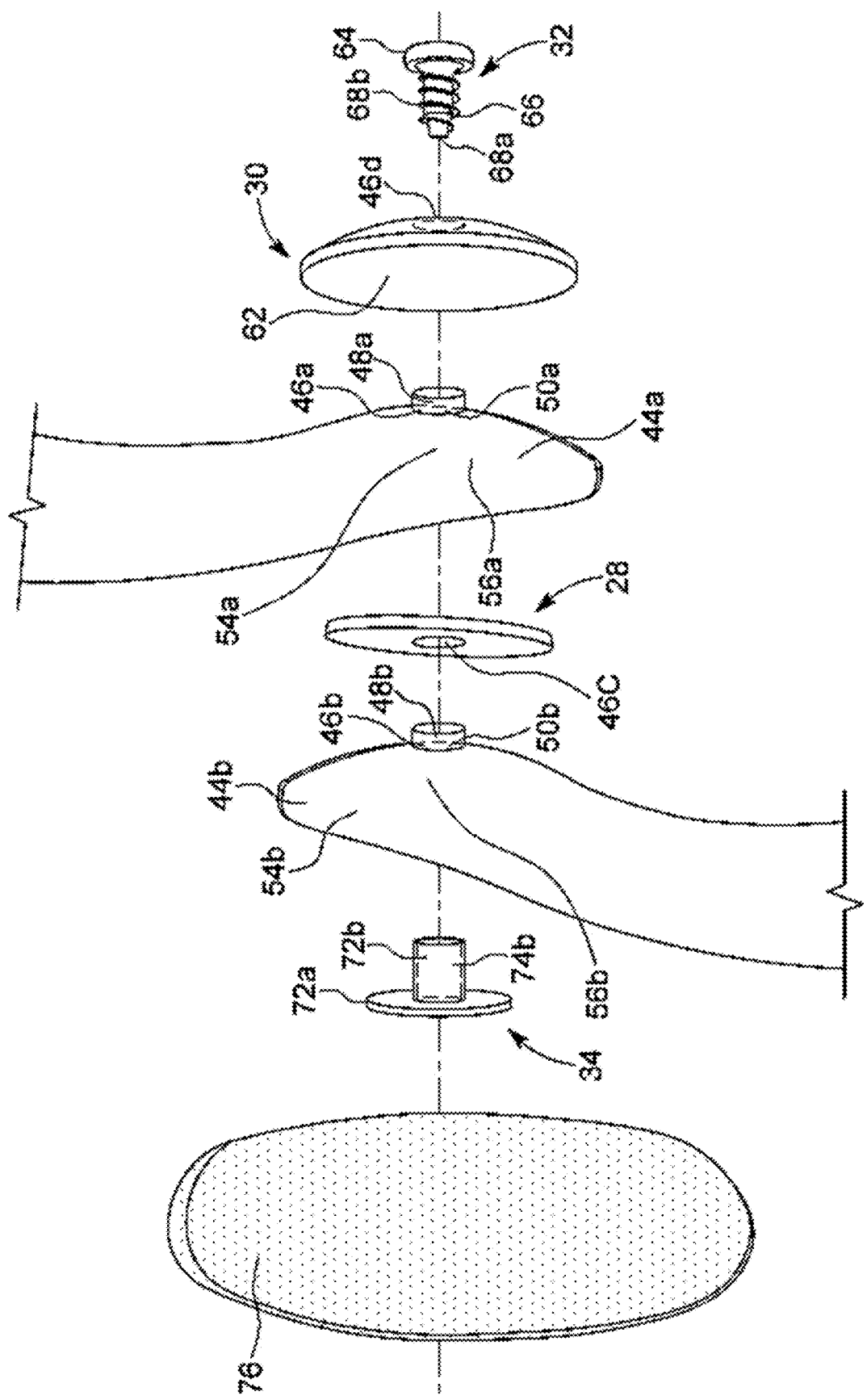
FIGS. 4A and 4B depict an exploded view and a detailed side view, respectively, of the innovative joint described herein.

In the preferred embodiment particularly shown in FIG. 4A, the bolt has a threaded shaft 68b in addition to the threaded distal end and the nut is a t-nut 72 having a flange 72a and barrel 72b that extends from the flange through the series of holes. The barrel of the nut has an internal threaded bore 74a which engages the threaded bolt along with a smooth outer surface 74b to allow the joint to freely pivot wherein the barrel at least partially extends through the aligned holes. In the preferred embodiment having a t-nut, the barrel extends through the respective holes in the distal ends of the thigh engaging section and the calf engaging section and further screws over more than one half of the length of the fully threaded shaft of the bolt.

In an alternative embodiment the bolt may be a shoulder bolt where a nut screws onto the threaded distal end along with another rigid washer positioned on the opposite side of the joint from the first rigid washer. Accordingly, it will be understood that other fasteners can be used in the joint to hold the washers and respective distal ends together while allowing the thigh section and calf section to pivot relative to the rotational axis of the fastener.

Although the curved distal ends of the thigh engaging section and the calf engaging section are intended to nest against one another with the flexible washer positioned there between, the preferred curvature includes a conical shape. As explained above, the rigid washer will therefore also have a conforming conical shape. In this embodiment the holes in each of the respective washers and distal ends of the orthosis sections are positioned at the tip of the cone which thereby forms a conical frustum. Accordingly, the multiple conical sections will nest within one another and be secured together by the fastener extending through the aligned holes.

Figure 3A:
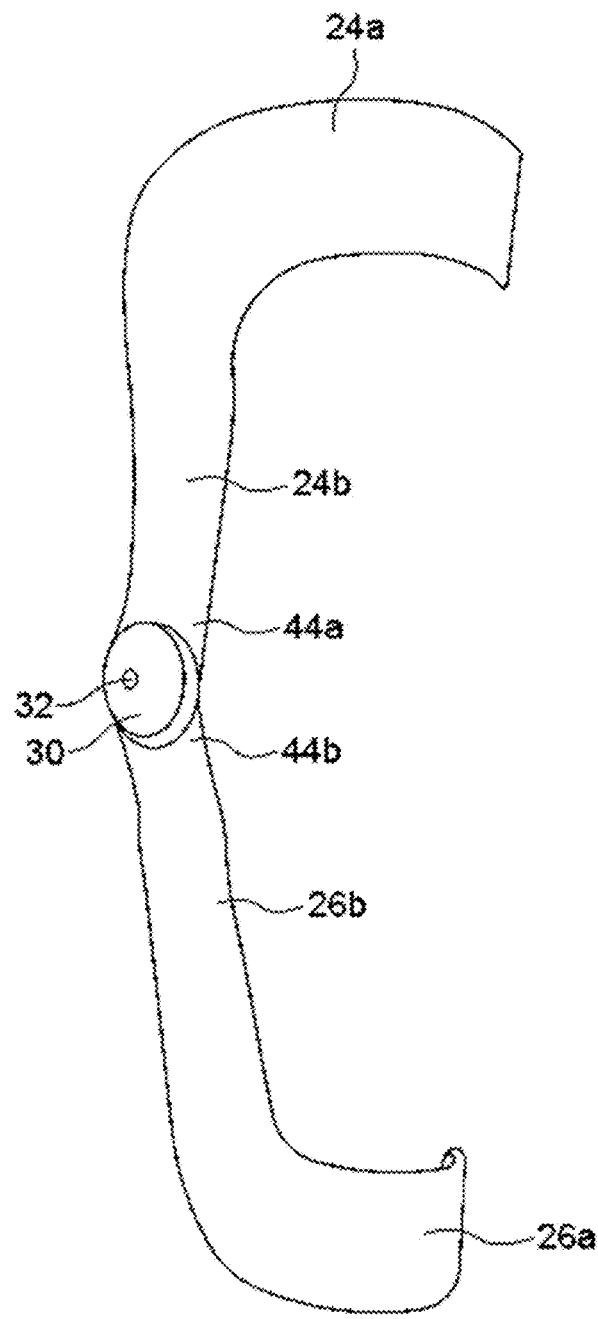
FIGS. 3A-3C are detail side views of an orthosis in a single-hinge configuration according to the inventive features described herein.
Figure 3B:
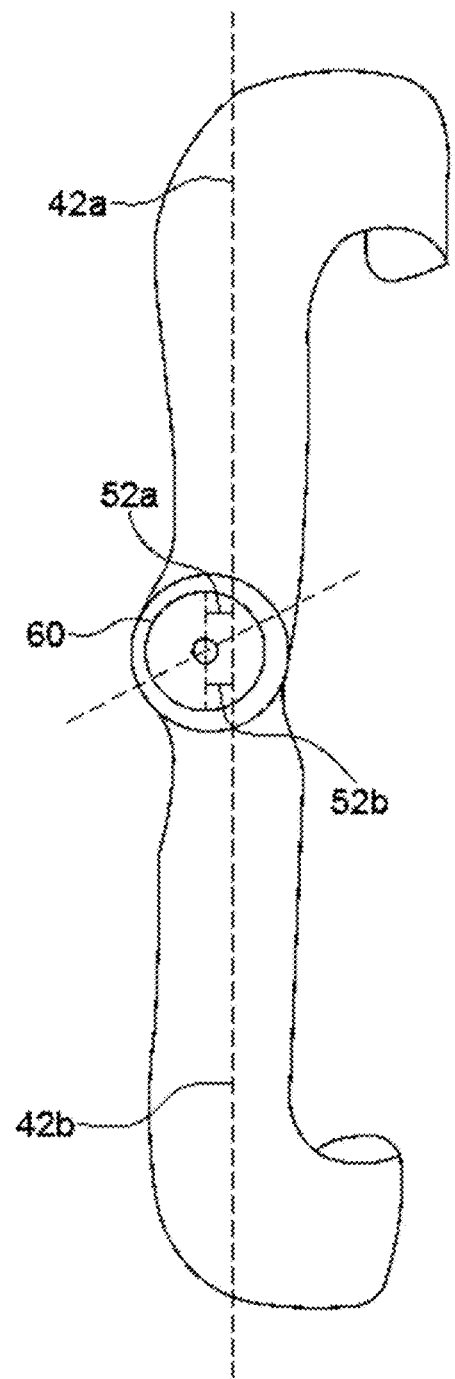
Figures 3C, 3D:
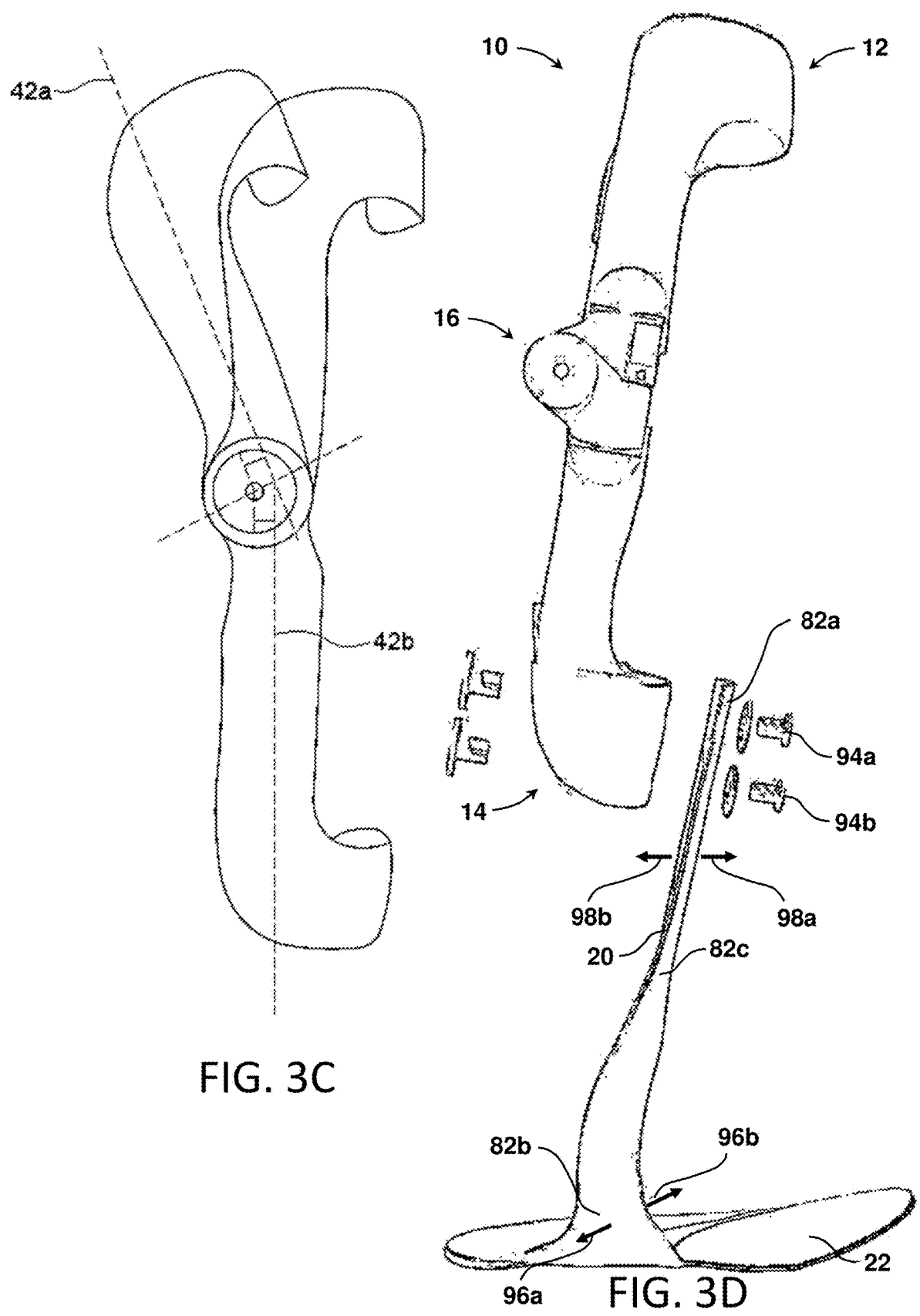
FIG. 3D is an exploded side view of an orthosis with a stirrup and a footplate in a double hinge configuration according to the inventive features described herein.

In another aspect of the joint described herein and as particularly shown in FIGS. 3B and 3C, the center point of each of the holes in the distal ends in the of the thigh engaging section and the calf engaging section are posteriorly offset from the longitudinal axis of the inferior side segment of the thigh engaging section and superior side segment of the calf engaging segment, respectively. The offset distance 52a and 52b is greater than the diameter 48a and 48b of the respective apertures in the distal ends of the thigh and calf sections, respectively. Accordingly, the joint is not only simplified and integrated with the thigh and calf portions of the orthosis, but the joint is also positioned posterior of the longitudinal axes to encourage knee extension as explained in detail below.

The orthosis' thigh engaging section and calf engaging section can be made from flexible unitary composite structure and the flexible washer is made from a flexible plastic. However, the rigid washer, bolt and nut are preferably made from a metal material to provide additional strength to the joint and extend the overall life of the joint. Since the metallic structure of these pieces can be uncomfortable against the knee of the wearer, a cushioning pad 76 is provided that covers the head of the bolt or nut that is proximate to the knee. Further, the padding thickness 78 can be increased to increase corrective three point pressure system for affected OA compartment as explained in detail below.

It should be appreciated that the joint can be positioned on both sides of the knee or on either the medial side of the knee or the lateral side of the knee without altering the function as described herein. Similarly, the distal end of the calf section may be positioned on the external side of the joint wherein the distal end of the thigh section is nested therein as opposed to the thigh section forming the outside of the joint as shown in FIG. 4A. Although these embodiments are not shown in the drawings, it will be understood by those having an ordinary skill in the art that the features that collectively form the simplified joint can be arranged in these alternative orientations and sufficiently provide an improved orthosis.

In another aspect of the knee orthosis shown in FIG. 2A, an adjustment strap 36a connects the medial superior side of the thigh engaging section to the lateral superior side of the thigh engaging section. Similarly, an adjustment strap 36b connects the medial inferior side of the calf engaging section to the lateral inferior side of the calf engaging section. Accordingly, the orthosis can be tightened or loosened by the adjustment straps as explained herein. Further, an additional adjustment strap 36c can be attached to the thigh posteriorly connect a top end of the superior anterior segment to further secure the orthosis to the wearer.

Figure 2C:
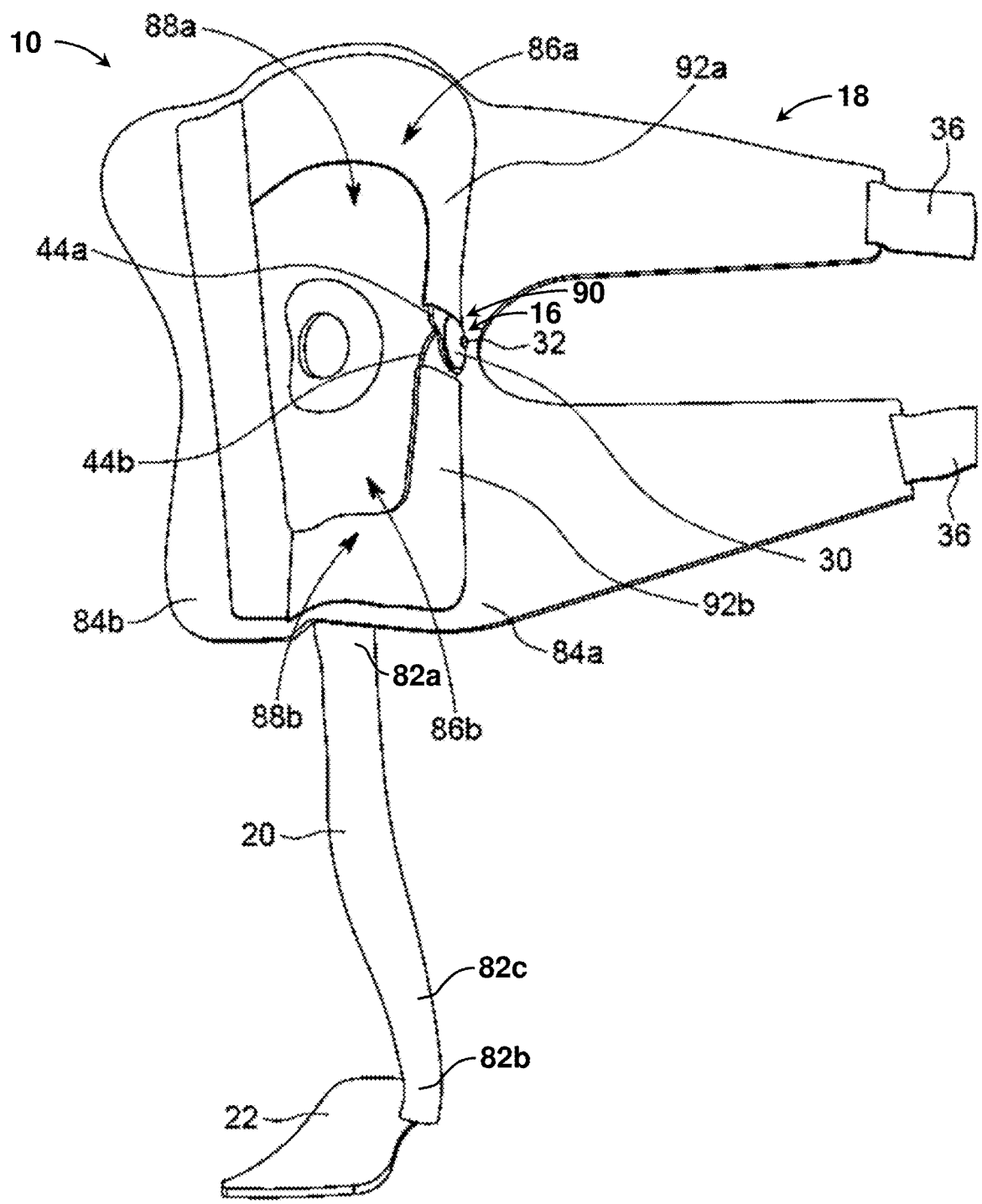
FIG. 2C is a front view of the orthosis with the stirrup and the footplate and a flexible wrap.

In the alternative embodiment shown in FIG. 2C, the flexible wrap 18 is used in conjunction with the adjustable straps and it is preferred that the wrap is used to provide additional stability when the orthosis is used without the stirrup and footplate describe below. The first side 84a of the flexible wrap has a portion 92a connected to the thigh engaging section and another portion 92b connected to the calf engaging section and is secured thereto with straps on the first side of the flexible wrap 36, as explained below. When connected and strapped with the adjustment strap, as shown in FIG. 2C, the wrap creates pockets 86a and 86b holding the thigh and calf sections in the respective openings 88a and 88b. Additionally, a space 90 is formed between the two pockets and the joint is positioned therein. Thus, the wrap does not interfere with the joint but holds the joint and orthosis against the leg and knee of the wearer.

To secure the orthosis a second side 84b of the wrap extends from the superior anterior segment of the thigh engaging section to the inferior anterior segment of the calf engaging section and folds around the posterior side of the thigh engaging section and the calf engaging section. Subsequently, the adjustment straps fold over the second side of the flexible wrap on the posterior side of the thigh engaging section and folds around to cover a portion of the first side on the anterior side of the thigh engaging section. Similarly, another adjustment strap folds over the flexible wrap on the posterior side of the calf engaging section and folds around to cover a portion of the pocket containing the calf section at an anterior side of the calf engaging section.

As indicated above, the particular knee ankle foot orthosis described herein, i.e. the KAFO device, includes the stirrup 20 and footplate 22 as shown in FIGS. 2, 3D, and 5. An upper fastener 94a and a lower fastener 94b are preferably used to securely and fixedly connect the proximal section 82a of the stirrup to a mounting section 80 on the inferior anterior segment of the calf section of the orthosis. It is important for the stirrup's proximal section to be positioned at the anterior portion of the orthosis' calf segment and to extend downward from the orthosis' calf segment in the coronal plane so that the stirrup can flex in the sagittal plane as the leg is moving forward during the mid-stance part of the gait. The stirrup is preferably formed as an elongated strip, i.e., a narrow and flat bar with the length greater than the width which is greater than the thickness ($T_S<L_S>W_S$, $W_S>T_S$), with a twisted section 82c between the proximal section and the distal section 82b so the stirrup's distal section is generally aligned with the sagittal plane where it is connected to the lateral side of the footplate. As shown in FIG. 3D, the stirrup's distal section can flex laterally 96a and medially 96b relative to the footplate during the gait cycle while the stirrup's proximal section flexes anteriorly 98a and posteriorly 98b relative to the orthosis' calf segment.

Preferably, the mounting section for the stirrup includes a buildup of composite layers on the inferior anterior segment with a series of apertures through which the fasteners 94 are secured. It will be appreciated that the stirrup can be connected to the orthosis by any number of means including a separate bracket assembly at the mounting section, adhesives and integrally forming the stirrup section with the orthosis. However, in the case where a separate bracket is used, it is preferred that the bracket can be adjusted relative to the orthosis to allow for a proper fit and positioning of the stirrup. It will also be appreciated that the stirrup may be removably attached to the orthosis or permanently affixed to the orthosis and may include a variable length section between the proximal end and distal end to alter the length of the stirrup and footplate from the bottom of the orthosis.

When creating the KAFO described herein, a mold is taken of a patient's leg using fiberglass tape, a 3D scan, or any other method for defining the shape and size of the leg. A stirrup is pre-selected from various different sizes and placed on the patient while the shape and size of the patient's leg is recorded. Subsequently, the stirrup is tested on the patient during gait observation to ensure fit and proper knee extension moment. The test stirrup is strapped around the calf at mid tibia. The lower section length and stirrup length are determined at this point by gait observation. If the patient encounters too much knee extension force, the stirrup length may be lengthened, and the stirrup width can be reduced with a grinder to reduce the force. Once the proper stirrup has been selected and trialed, the leg is elevated or the patient stands and the mold is taken over the stirrup. The mold is removed and turned into a plaster or foam mold or a 3D model to be modified with relief on the tibial crest or any other areas that may not tolerate extension forces. Alternatively, the negative mold can be created by a 3D scanner and modified using computer aided design (CAD) software before the positive is formed by a multi axis carver. Further, the hinge, frame and stirrup may also be printed on a 3D printer. Once the mold has been created, the KAFO is preferably fabricated using composite lamination or 3D printing techniques.

In selecting the material(s) to manufacture the stirrup according to the for the preferred elongated bar shape as disclosed herein, the stirrup material preferably has a stiffness with a Young's modulus of approximately 10 GPa. For a given material stiffness and cross-sectional bar shape for the stirrup, i.e., the width and thickness of the stirrup, the different stirrup lengths have an inverse relationship on the spring constant such that the shorter stirrup lengths resulting in the higher spring constants. For example, for a KAFO in which the knee's hinge point is spaced from the bottom of the footplate by a total thirteen inches (13"), the spring constant for a stirrup with a bar cross-section is presented in Table 3 below for a set of corresponding lengths of the stirrup ($L_S$) and the orthosis' calf section ($L_C$). Accordingly, the relative lengths of the stirrup and the orthosis' calf section are important aspects to consider when sizing the KAFO to the patient.

TABLE 3

Stirrup Spring Constants

| Stirrup Length- $L_S$ (in) | Calf Section Length- $L_C$ (in) | Force (N) per Inch Displacement | Spring Constant (N/m) |
|---|---|---|---|
| 9 | 4 | 6.7 | 264 |
| 8 | 5 | 6.9 | 272 |
| 7 | 6 | 7.2 | 283 |
| 6 | 7 | 7.7 | 303 |
| 5 | 8 | 8.4 | 331 |
| 4 | 9 | 9.3 | 366 |

The stirrup is dynamic and provides forces in the sagittal plane to control knee buckling. This stored energy return is directed to the knee joint through the attachment of the stirrup and lower section to the upper knee section. As explained in detail above with regard to the raw stirrup forces in Table 1, the normalized stirrup forces in Table 2, and the stirrup spring constants in Table 3, the length of the orthosis' calf section ($L_C$) and the length of the stirrup ($L_S$) impact the stored energy in the stirrup according to the mechanical properties of the design. The stirrup controls ankle dorsiflexion collapse and substitutes for the weak plantar flexor muscles, and subsequently the orthosis controls knee buckling.

Figure 4B:
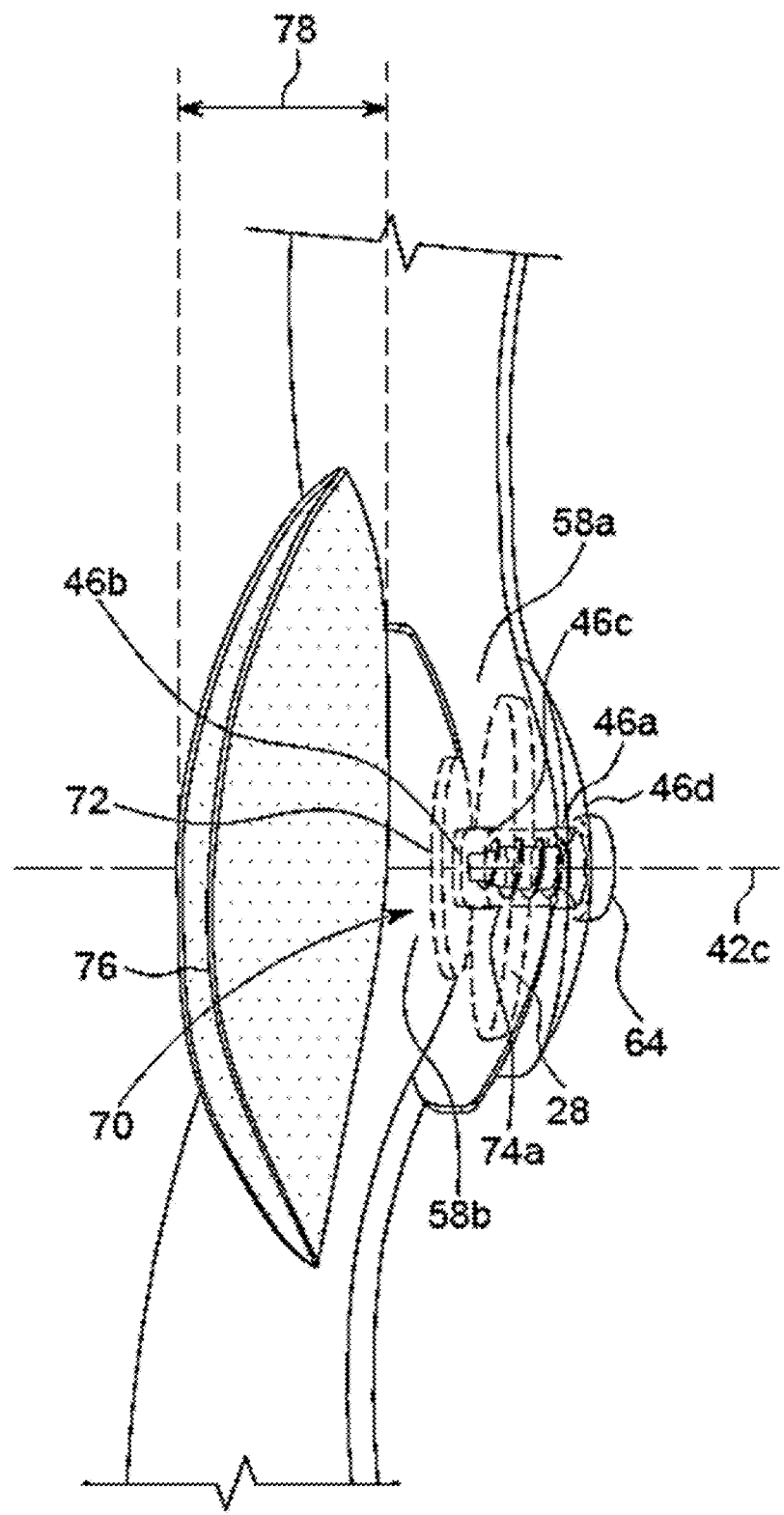

As shown in FIGS. 4A and 4B, at a normal stance pre-buckle a patient's knee will generally have an angle of approximately 0° degrees with the ankle being angled 900 from the leg. During a buckle, the knee may flex to an angle of 200 and the ankle will move from 900 to an angle greater than 15°. To control this buckling the hinge described herein is biased towards the posterior side of the knee joint in a position that encourages knee extension. Additionally, the dynamic stirrup flexes during normal gait and thereby stores energy which ultimately is excreted on the hinge and the knee into an extension. As these stored forces extend the hinge and knee joint, the footplate also prevents the angle of the ankle's dorsi flexion from exceeding 10°. Thus, knee buckling is passively controlled without the need of a locking hinge.

The hinge is light weight and uses a small stainless conical washer to reinforce the outside of the hinge, a nylon washer between the joint and a t-nut and screw to hold the hinge together. However, the orthosis described herein has a generally stiff stirrup but when it flexes during normal gait it stores energy and returns the energy with a force directed into knee extension as describe above. Accordingly, this force controls knee buckling. Although the proper stiffness of the stirrup will vary between patients, the stirrup can be properly fitted and stiffness can be altered by shortening the length of stirrup to increase force or decreasing the width of the stirrup to reduce stiffness. In making such adjustments the design must take into consideration patient height, weight, activity level and to what degree the knee of the patient is buckling. In fine tuning the KAFO to the patient, the extension forces produced by the stirrup can be reduced after the KAFO has been fabricated by griding or otherwise removing material from the width of the stirrup. As indicated above, the dynamic force around the ankle controls dorsiflexion and acts as a substitute for the weak plantar flexors and thus controls knee buckling.

Another advantage over any existing orthosis is that the KAFO described herein is stiff where appropriate and flexible where needed. The entire orthosis stores energy and does not incorporate a mechanical lock at the knee or ankle to prevent knee buckling. Accordingly, the orthosis not only controls buckling through the dynamic design but also allows functional range of motion at the knee and ankle.

The orthosis is made up of a U-shaped dynamic upper section having a medial upper side a lateral upper side which extend from a top end proximate to the upper thigh to a bottom end near the top most part of the knee joint for a single joint configuration. On the double joint configuration, the medial upper side will also extend down to end at the top most part of the knee joint on the opposite side of the orthosis. Alternatively, the orthosis could be made of an L-shaped design when the flexible wrap is used for a single joint configuration, as shown in FIGS. 3A and 3B. The pair of upper sides are connected at their top end by an anterior upper section which extends around the front of the thigh. In operation, this anterior upper section functions to apply a counter force during normal gait to extend the knee and subsequently helps the stirrup control buckling. Additionally, a securing strap may extend from the top end of the upper sides posteriorly around the back of the thigh to hold the orthosis in place.

In addition to the upper section, the orthosis has a matching lower section with a medial lower side and a lateral lower side positioned on opposite sides of the patient's upper calf. The pair of lower sides accordingly extend from a top end just below the knee joint to a bottom end a distance down the leg of the patient. For the double joint configuration, both the medial lower side and the lateral lower side extend upward to the corresponding medial knee joint and lateral knee joint, respectively. Similar to the upper section above, the lower section has an anterior lower section connecting the pair of sides on the front of the leg. Of course, this anterior lower section also provides a counter force during normal gait to aid in extending the knee joint and thereby controlling buckling.

The rigid hinge is positioned between the upper and lower section on one side of the knee for the single joint configuration and on both sides of the knee for the double joint configuration and accordingly connects the upper and lower sections at the medial sides and/or lateral sides. In operation, the upper section, lower section and hinge can function to apply three corrective forces on the knee of the patient. As shown in FIG. 2A, force is applied through the superior thigh section as indicated by arrow $F_S$, through the inferior calf section indicated by arrow $F_I$, and through the hinge indicated by arrow $F_H$. Further, the conical shape of the hinge provides a benefit over hinges in the prior art where the curved shape reduces the likelihood of bushing wear and hinge failure.

Although it may seem intuitive to incorporate a standard foot and ankle orthosis (AFO) into a knee orthosis (KO) to create a KAFO to control knee buckling, such a combination would fail to work satisfactorily without the innovations of the present invention. First, any KAFO needs to be designed as a complete unit to account for all the angles of the knee and ankle in all three (3) planes of motion. Merely combining an AFO with a KO would produce an undesirable result. For example, US Pat. App. Pub. No. 2009/0198166 by Shlomovitz has a pivot point located at the top anterior portion of the calf section of the AFO which necessarily allows the proximal end of the stirrup to rotate relative to the calf section. This rotation of the stirrup's proximal end prevents the stirrup from storing sufficient energy to provide the force that is required to control knee buckling. Rather than have the proximal end of the stirrup extend straight down from the anterior portion of the orthosis' calf section as in the present invention, Shlomovitz has the proximal end of the stirrup first extending laterally to the lateral side of the orthosis' calf section and then extending downward to the lateral side of the footplate which allows for the unimpeded rotation of the stirrup relative to the orthosis' calf section according to the teaching of Shlomovitz. If the pivot point was removed and the stirrup extended straight down from the anterior face of the orthosis' calf section in the Shlomovitz AFO, the stirrup would be impeded from rotating and the operation of the Shlomovitz AFO would change to the point that it no longer would function according to its intended purpose, and the design would fail.

The primary improvement of the KAFO of the present invention is the dynamic stirrup that extends from the orthosis' lower section to a footplate positioned below the foot of the patient. The stirrup accordingly has a proximal end attached to the midpoint of the anterior section of the lower section and distal end connected to the footplate described above. Additionally, the stirrup extends anteriorly around the lateral malleolus of the ankle joint of the patient an accordingly controls buckling. In operation, the combination of the upper section, lower section and stirrup store energy on the upper knee, the lower ankle and foot section to control knee buckling by providing counter forces that extend the knee during the gait cycle, particularly at the mid-stance.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. For example, the particular KAFO shown and described with respect to the present invention is a full leg orthosis that is used for treating unicompartment knee osteoarthritis (OA) by decompressing axial forces using a three-point pressure system around the knee. It will be appreciated that the inventive dynamic storing and redirecting of forces using the stirrup during the gait cycle can be incorporated into most full leg orthosis designs regardless of whether or not the orthosis treats OA. Thus, the breadth and scope of the present invention should not be limited by any of the above-described exemplary embodiments, but should be defined only in accordance with the following claims appended hereto and their equivalents.

What is claimed is:

1. A knee ankle foot orthosis positioned on a leg of a person relative to a knee joint, comprising:
   a thigh engaging section comprising a superior anterior segment, an inferior side segment, a medial superior side, and a lateral superior side, wherein the inferior side segment has a first longitudinal axis, wherein the inferior side segment has a first distal end comprising a first aperture with a first diameter and a first center, wherein the first center of the first aperture is posteriorly offset from the first longitudinal axis by a first distance greater than the first diameter, and wherein the first distal end of the inferior side segment surrounding the first aperture is further comprised of a first curved segment with a first convex outer surface and a first concave inner surface;

a calf engaging section comprising an inferior anterior segment, a superior side segment, a medial inferior side, and a lateral inferior side, wherein the superior side segment has a second longitudinal axis, wherein the superior side segment has a second distal end comprising a second aperture with a second diameter and a second center, wherein the second center is aligned with the first center, wherein the second center of the second aperture is posteriorly offset from the second longitudinal axis by a second distance greater than the second diameter, wherein the second distal end of the superior side segment surrounding the second aperture is further comprised of a second curved segment with a second convex outer surface and a second concave inner surface, and wherein the second curved segment is conformal with the first curved segment;

a fastener extending through the first aperture and the second aperture along a third longitudinal axis, wherein the fastener connects the first distal end of the thigh engaging section and the second distal send of the calf engaging section as a hinge joint around which the thigh engaging section and the calf engaging section rotate around the third longitudinal axis posteriorly from the first longitudinal axis and the second longitudinal axis by the first distance and the second distance, respectively;

a first adjustment strap connecting the medial superior side to the lateral superior side in the thigh engaging section;

a second adjustment strap connecting the medial inferior side to the lateral inferior side in the calf engaging section;

a stirrup extending between a proximal section and a distal section, wherein the proximal section is fixedly connected to the inferior anterior segment of the calf engaging section, wherein the proximal section longitudinally extends past the inferior anterior segment of the calf engaging section in a coronal plane with the inferior anterior segment of the calf engaging section, wherein the proximal section does not laterally extend to the medial inferior side or the lateral inferior side of the calf engaging section, and wherein the proximal section of the stirrup does not rotate relative to the calf engaging section at the inferior anterior segment while the distal end of the stirrup bends relative to the proximal end of the stirrup; and a footplate connected to the distal section of the stirrup.

2. The knee ankle foot orthosis of claim 1, wherein the thigh engaging section is a flexible unitary composite structure, and wherein the calf engaging section is a flexible unitary composite structure.

3. The knee ankle foot orthosis of claim 1, wherein the stirrup is further comprised of a twisted section turning laterally to the distal section from the proximal section.

4. The knee ankle foot orthosis of claim 3, wherein the stirrup's distal section is aligned in a sagittal plane substantially perpendicular to the coronal plane of the proximal section.

5. The knee ankle foot orthosis of claim 4, wherein the distal section connects to the lateral side of the footplate, and wherein the bending of the stirrup applies a posterior directed force in the sagittal plane to the inferior anterior segment of the calf engaging segment during a mid-stance of a gait.

6. The knee ankle foot orthosis of claim 1, wherein the stirrup has a bar cross-sectional shape with a width greater than a thickness, and wherein a length of the stirrup is greater than the width.

7. The knee ankle foot orthosis of claim 6, wherein the stirrup has a weight normalized moment in the range between 0.4 and 2.0, inclusive.

8. The knee ankle foot orthosis of claim 6, wherein the stirrup has a spring constant in the range between 200 N/m to 400 N/m.

9. The knee ankle foot orthosis of claim 1, further comprising a flexible wrap connected to the thigh engaging section and the calf engaging section, wherein the first adjustment strap and the second adjustment strap extend from a first side of the flexible wrap.

10. The knee ankle foot orthosis of claim 1, wherein the fastener is further comprised of a flexible washer, a rigid washer, a bolt, and a nut, wherein the flexible washer is positioned between the conforming curved segments of the first distal end and the second distal end of the thigh engaging section and the calf engaging section, respectively, wherein the flexible washer has a third aperture aligned with the first aperture and the second aperture, wherein the rigid washer is located on an external side of the thigh engaging section and the calf engaging section, wherein the rigid washer has a curved shape conforming with and covering the curved segments of the first distal end and the second distal end of the thigh engaging section and the calf engaging section, respectively, wherein the rigid washer has a fourth aperture aligned with the first aperture, the second aperture, and the third aperture, wherein the bolt is comprised of a head, a shaft, and a threaded distal end, wherein the head is engaged with the rigid washer, wherein the shaft extends through the first aperture, the second aperture, the third aperture, and the fourth aperture along a third longitudinal axis, wherein the threaded distal end extends toward an internal side of the thigh engaging section and the calf engaging section, wherein the thigh engaging section and the calf engaging section rotate relative to each other around the third rotational axis, and wherein the nut is screwed onto the threaded distal end of the bolt at the internal side of the thigh engaging section and the calf engaging section.

11. A knee ankle foot orthosis positioned on a leg of a person relative to a knee joint, comprising:

a thigh engaging section comprising a superior anterior segment, an inferior side segment, a medial superior side, and a lateral superior side;

a calf engaging section comprising an inferior anterior segment, a superior side segment, a medial inferior side, and a lateral inferior side;

a hinge joint connecting the inferior side segment of the thigh engaging section with the superior side segment of the calf engaging section, wherein the thigh engaging section and the calf engaging section rotate relative to each other around the hinge joint;

a first adjustment strap connecting the medial superior side to the lateral superior side in the thigh engaging section;

a second adjustment strap connecting the medial inferior side to the lateral inferior side in the calf engaging section;

a stirrup extending between a proximal section and a distal section, wherein the stirrup is further comprised of a twisted section turning laterally to the distal section from the proximal section, wherein the proximal section is fixedly connected to the inferior anterior segment of the calf engaging section, wherein the proximal section longitudinally extends past the inferior anterior segment of the calf engaging section in a coronal plane with the inferior anterior segment of the calf engaging section, wherein the proximal section does not laterally extend to the medial inferior side or the lateral inferior side of the calf engaging section, wherein the proximal section of the stirrup does not rotate relative to the calf engaging section at the inferior anterior segment while the distal end of the stirrup bends relative to the proximal end of the stirrup; and a footplate, wherein a lateral side of the footplate is connected to the distal section of the stirrup.

12. The knee ankle foot orthosis of claim 11, wherein the distal section of the stirrup is aligned in a sagittal plane substantially perpendicular to the coronal plane of the proximal section, and wherein the bending of the stirrup applies a posterior directed force in the sagittal plane to the inferior anterior segment of the calf engaging segment during a mid-stance of a gait.

13. The knee ankle foot orthosis of claim 11, wherein the stirrup has a bar cross-sectional shape with a width greater than a thickness, and wherein a length of the stirrup is greater than the width.

14. The knee ankle foot orthosis of claim 13, wherein the stirrup has a weight normalized moment in the range between 0.4 and 2.0, inclusive.

15. The knee ankle foot orthosis of claim 13, wherein the stirrup has a spring constant in the range between 200 N/m to 400 N/m.

16. A knee ankle foot orthosis positioned on e leg of a person relative to a knee joint, comprising:
- a thigh engaging section comprising a superior anterior segment, an inferior side segment, a medial superior side, and a lateral superior side;
- a calf engaging section comprising an inferior anterior segment, a superior side segment, a medial inferior side, and a lateral inferior side;
- a hinge joint connecting the inferior side segment of the thigh engaging section with the superior side segment of the calf engaging section, wherein the thigh engaging section and the calf engaging section rotate relative to each other around the hinge joint;
- a first adjustment strap connecting the medial superior side to the lateral superior side in the thigh engaging section;
- a second adjustment strap connecting the medial inferior side to the lateral inferior side in the calf engaging section;
- a stirrup extending between a proximal section and a distal section, wherein the stirrup is further comprised of a twisted section turning laterally to the distal section from the proximal section, wherein the distal section of the stirrup is aligned in a sagittal plane substantially perpendicular to the coronal plane of the proximal section, wherein the stirrup has a bar cross-sectional shape with a width greater than a thickness, wherein a length of the stirrup is greater than the width, wherein the proximal section is fixedly connected to the inferior anterior segment of the calf engaging section, wherein the proximal section longitudinally extends past the inferior anterior segment of the calf engaging section in a coronal plane with the inferior anterior segment of the calf engaging section, wherein the proximal section does not laterally extend to the medial inferior side or the lateral inferior side of the calf engaging section, wherein the proximal section of the stirrup does not rotate relative to the calf engaging section at the inferior anterior segment while the distal end of the stirrup bends relative to the proximal end of the stirrup; and
- a footplate connected to the distal section of the stirrup.

17. The knee ankle foot orthosis of claim 16, wherein the distal section of the stirrup connects to a lateral side of the footplate.

18. The knee ankle foot orthosis of claim 16, wherein the stirrup has a weight normalized moment in the range between 0.4 and 2.0, inclusive.

19. The knee ankle foot orthosis of claim 16, wherein the stirrup has a spring constant in the range between 200 N/m to 400 N/m.

20. The knee ankle foot orthosis of claim 16, wherein the bar cross-sectional shape of the stirrup is substantially the same along its length in the proximal section, the twisted section, and the distal section, and wherein a bending of the stirrup applies a posterior directed force in the sagittal plane to the inferior anterior segment of the calf engaging segment during a mid-stance of a gait.

* * * * *